US012112836B2

(12) United States Patent
Bowden, Jr. et al.

(10) Patent No.: US 12,112,836 B2
(45) Date of Patent: Oct. 8, 2024

(54) ARTIFICIAL INTELLIGENCE DIRECTED ZEOLITE SYNTHESIS

(71) Applicant: Chevron U.S.A. Inc., San Ramon, CA (US)

(72) Inventors: Larry A. Bowden, Jr., Houston, TX (US); Dan Xie, El Cerrito, CA (US); Christopher Michael Lew, Almeda, CA (US); Joel Edward Schmidt, Oakland, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 787 days.

(21) Appl. No.: 17/346,463

(22) Filed: Jun. 14, 2021

(65) Prior Publication Data

US 2022/0399085 A1      Dec. 15, 2022

(51) Int. Cl.
*G16C 20/70* (2019.01)
*G16C 20/10* (2019.01)
(Continued)

(52) U.S. Cl.
CPC ............. *G16C 20/70* (2019.02); *G16C 20/10* (2019.02); *G16C 20/40* (2019.02); *G16C 20/50* (2019.02); *G16C 60/00* (2019.02); *B01J 29/04* (2013.01)

(58) Field of Classification Search
CPC ........ G16C 20/70; G16C 20/10; G16C 20/40; G16C 20/50; B01J 29/04
See application file for complete search history.

(56) References Cited

U.S. PATENT DOCUMENTS 5,625,750 A    4/1997   Puskorius
5,774,381 A *  6/1998   Meier .................. B01J 8/001
                                                      703/2

(Continued)

FOREIGN PATENT DOCUMENTS

KR     20090102592      9/2009
KR     20200096452      8/2020

OTHER PUBLICATIONS

S. Yang et al., Identifying Zeolite Frameworks With a Machine Learning Approach, 2009, J. Phys. Chem. C 113:21721-21725.

(Continued)

*Primary Examiner* — David E Choi
(74) *Attorney, Agent, or Firm* — King & Spalding LLP

(57) ABSTRACT

A computer implemented method for designing chemical reactions for catalyst construction is described. The method includes extracting historical data including historic chemical reaction data and historic catalyst construction yield data and converting the historic chemical reaction data into graph models to represent molecular structure data. The method also includes incorporating the graph models into a chemical reaction algorithm and training a vectorized cognitive deep learning network of the chemical reaction algorithm by using the graph models and a property of the historic chemical reaction data to produce a catalyst chemical reaction model. Further, the method includes validating the catalyst chemical reaction model by inputting the historic chemical reaction data and comparing a generated property corresponding to the catalyst chemical reaction model to the property of the historic chemical reaction data. Lastly, the method includes updating the training of the catalyst chemical reaction model.

20 Claims, 9 Drawing Sheets

(51) Int. Cl.
*G16C 20/40* (2019.01)
*G16C 20/50* (2019.01)
*G16C 60/00* (2019.01)
*B01J 29/04* (2006.01)

(56) References Cited

U.S. PATENT DOCUMENTS

| | | | |
|---|---|---|---|
| 6,081,766 A | 6/2000 | Chapman | |
| 11,732,632 B1* | 8/2023 | Ethington | F01N 11/002 60/277 |
| 2008/0170987 A1* | 7/2008 | Lewis | B01J 29/70 423/718 |
| 2017/0316487 A1* | 11/2017 | Mazed | G06Q 30/0241 |
| 2020/0168300 A1* | 5/2020 | Goddard, III | B01J 23/745 |
| 2020/0234798 A1 | 7/2020 | Denmark et al. | |
| 2020/0263594 A1 | 8/2020 | Muto et al. | |
| 2020/0327476 A1* | 10/2020 | Shi | G05B 13/0265 |
| 2020/0391721 A1* | 12/2020 | Wang | B60W 10/06 |
| 2022/0044766 A1* | 2/2022 | Toniato | G06N 5/04 |
| 2022/0143569 A1* | 5/2022 | Holzmeister | G05B 19/41885 |
| 2022/0383994 A1* | 12/2022 | Rabideau | G16C 20/70 |
| 2022/0399085 A1* | 12/2022 | Bowden, Jr. | G16C 60/00 |

OTHER PUBLICATIONS

Jensen, Zach, et al., A Machine Learning Approach to Zeolite Synthesis Enabled by Automatic Literature Data Extraction, 2019, ACS Cent. Science, 5: 892-899.

Molner, M., et al., Machine Learning Applied to Zeolite Synthesis: The Missing Link, 2019, Accounts of Chem. Research, 52: 2971-2980.

Kim, B., et al., Inverse Design Oof Porous Materials Using Artificial Neural Networks, 2020, Science Advances, 6: eaax9324.

Williams, Travis, et al., Enabling Catalyst Discovery Through Machine Learning and High-Throughput Experimentation, 2020, Chemistry of Materials, 32: 157-165.

Gaillac, Romain, et al., Speeding Up Discovery of Auxetic Zeolite Frameworks by Machine Learning, 2020, Chemistry of Materials, 32:2653-2663.

International Search Report for PCT/US2022/033284 dated Aug. 30, 2022.

* cited by examiner

ARTIFICIAL INTELLIGENCE DIRECTED ZEOLITE SYNTHESIS

TECHNICAL FIELD

The present disclosure relates generally to artificial intelligence (AI) assisted catalyst production. In particular, using AI to direct modeling, design, and construction of zeolite materials.

BACKGROUND

Zeolites are microporous, crystalline aluminosilicate materials with a wide range of applications including catalysis, adsorption, and ion exchange in the oil and gas industry. A crystallization of the zeolite often occurs through a hydrothermal synthesis governed by a large number of synthesis parameters and complex crystallization kinetics that yield desired zeolite structures. The zeolite synthesis-structure relationships are difficult to understand due to these complexities and the methodologies for predicting zeolite structures from synthesis parameters are currently limited. The lack of predictive ability to computationally design zeolite synthesis routes limits the efficiency of the current zeolite synthesis and design process and hinders deploying of new and advanced zeolite catalysts. Moreover, there is a need to design and construct zeolite catalysts for specific chemical reactions, molecular adsorptions, and diffusions for the oil and gas industry.

Recent advances in AI with increased accessibility to large data sets and the ability to include and process smaller private experimental data sets allow the development of new machine learning (ML) algorithms capable of extracting relationships between the synthesis and the zeolite structure. ML has already revolutionized many areas in materials construction by enhancing abilities to map synthesis recipes and processes to product properties, especially in an absence of well-understood mechanisms. Considering the large volume of synthesis records in public and from private practice, the use of ML approaches to assist zeolite synthesis is especially timely.

In addition, along with a need for high yield zeolite construction and unlike many other materials science domains, the zeolite community often includes failed syntheses in publications and data sets, which makes AI assisted zeolite synthesis more promising. Therefore, AI directed zeolite synthesis and construction by using ML algorithms and models would be beneficial.

SUMMARY

The present disclosure relates generally to computer implemented methods for AI directed zeolite synthesis. One example includes a computer implemented method for designing of chemical reactions for catalyst construction. In an example embodiment, the method includes extracting historical data including historic chemical reaction data and historic catalyst construction yield data and converting the historic chemical reaction data into graph models to represent molecular structure data. The method also includes incorporating the graph models representing the molecular structure data into a chemical reaction algorithm and training a vectorized cognitive deep learning network of the chemical reaction algorithm by using the graph models and a property (e.g., chemical, physical, or desired) of the historic chemical reaction data to produce a catalyst chemical reaction model. Further, the method includes validating the catalyst chemical reaction model by inputting the historic chemical reaction data and comparing a property generated by the catalyst chemical reaction model to that of the historic chemical reaction data. Lastly, the method includes updating the training of the catalyst chemical reaction model based on a difference between the generated property and that of the historic chemical reaction data being larger than a threshold value.

In another example embodiment, a computer implemented method for constructing a catalyst structure includes extracting historic catalyst production information from operational history. The method also includes constructing, based on the historic catalyst production information, graph data representing synthesis recipes and processes for catalyst production. Further, the method includes training a neural network of a catalyst production algorithm by using the graph data to generate a catalyst production model. Lastly, the method includes validating the catalyst production model by inputting the graph data and comparing a catalyst generated from the catalyst production model with catalyst corresponding to the synthesis recipes and processes in the graph data.

In another example embodiment, an artificial intelligence assisted catalyst processing method is implemented by a computer. The method includes designing chemical reactions by training a vectorized cognitive deep learning network of a chemical reaction algorithm and inputting raw chemical reactants data and desired catalyst product properties to a chemical reaction model generated from the training of the chemical reaction algorithm. The method also includes designing a catalyst structure based on the chemical reactions that are designed in accordance with a maximum catalyst production yield and corresponding catalyst product formulations. The method further includes producing the catalyst structure automatically by forwarding catalyst production information to a production line, wherein the catalyst production information is generated by inputting the chemical reactions that were designed and the catalyst structure that was designed into a catalyst production model.

These and other aspects, objects, features, and embodiments will be apparent from the following description and the appended claims. The foregoing summary is provided to introduce various concepts in a simplified form that are further described below in the detailed description. This summary is not intended to identify required or essential features of the claimed subject matter nor is the summary intended to limit the scope of the claimed subject matter.

BRIEF DESCRIPTION OF THE DRAWINGS

Reference will now be made to the accompanying drawings, which are not necessarily drawn to scale, and wherein.

Figure 1:
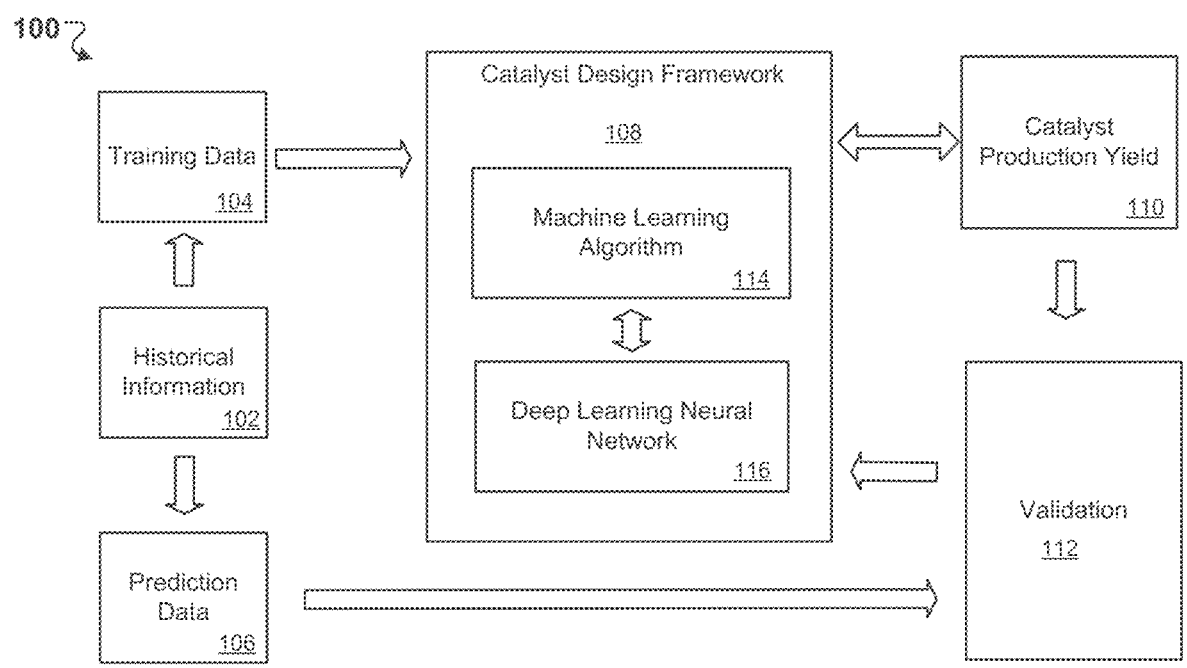
FIG. 1 illustrates an example workflow of designing chemical reactions for catalyst construction by a machine learning algorithm.

The drawings illustrate only example embodiments and are therefore not to be considered limiting in scope. The elements and features shown in the drawings are not necessarily to scale, emphasis instead being placed upon clearly illustrating the principles of the example embodiments. Additionally, certain dimensions or placements may be exaggerated to help visually convey such principles. In the drawings, the same reference numerals used in different embodiments designate like or corresponding, but not necessarily identical, elements.

DETAILED DESCRIPTION OF EXAMPLE EMBODIMENTS

In the following paragraphs, particular embodiments will be described in further detail by way of example with reference to the drawings. In the description, well-known components, methods, and/or processing techniques are omitted or briefly described. Furthermore, reference to various feature(s) of the embodiments is not to suggest that all embodiments must include the referenced feature(s).

Catalyst construction generally is a tacit knowledge and requires research and investment on catalyst design processes for explicit understandings. Efficient catalyst study can be achieved at lower costs by utilizing ML approaches to train cognitive models in extracting relationships between the synthesis and catalyst production structures. The cognitive models are configured to simulate chemical reactions with corresponding production yields. In addition, these models can be interrogated in suggesting catalyst formulations for specific chemical reactions. There is a need to further synthesize and construct zeolite catalysts because their chemical structure is complex, and it is hard to predict zeolite structure merely according to synthesis parameters.

The zeolite synthesis and design processes usually include multiple steps that are manually intensive and time consuming. To improve the efficiency of these processes, this invention designs zeolite structures with the assistance of ML algorithms and models. In one example embodiment, this ML approach uses a vectorized cognitive deep learning neural network to generate a catalyst design model for the zeolite design. This vectorized cognitive deep learning neural network receives graph representations of molecular structures of materials involved in the zeolite chemical reactions as input and generates zeolite catalyst yield as a prediction result. Specifically, the graph representation inputs include nodes with atomic properties and edge connections representing intermolecular properties, e.g., chemical bond angles. This invention also incorporates statistical and probabilistic methods into the catalyst design model to address undetermined geometries and tilings characteristics of zeolite crystals that do not have fixed structures when the zeolite crystals form and grow. The zeolite formulations are created in accordance with a maximum catalyst construction yield or selectivity output from the ML models. The catalyst selectivity data may not be available in the literature but is available for the ML models trained with internal data.

This invention further includes a ML approach to improve the zeolite construction process efficiency by utilizing robotics to automate the catalyst construction process. The automatic zeolite construction process can be generated from a digital fingerprint of a catalyst construction model that designs the zeolite construction recipe from historical production data, available catalyst structure, and organic structure directing agents for the synthesis.

Turning now to the drawings, FIG. 1 illustrates an example workflow 100 of designing chemical reactions for catalyst construction by a ML algorithm 114. The workflow 100 is configured to provide training data 104 to the catalyst design framework 108 for training of the deep learning neural network 116 located therein in order to generate prediction models for catalyst production yield prediction. The resulting chemical reaction model for catalyst design is further provided for validation 112 under various chemical reaction conditions of the catalyst. Further, results of the validation 112 are fed back to the catalyst design framework 108 to further optimize the ML algorithm 114 in improving its accuracy for the catalyst yield prediction. This workflow 100 also includes providing prediction data 106 to the trained ML algorithm 114 to evaluate the accuracy of the resulting prediction model by comparing the results of catalyst production yield 110 generated from the prediction model with actual prediction data 106.

In an example embodiment, the workflow 100 includes inputting data 102 for the prediction of catalyst chemical reaction. The input data may be historical information collected from production history of the catalyst in a factory. In addition, the input data may be pulled from laboratory data, operation log data, literature reports, or open access data sets and synthesis protocols that reveal catalyst production yield of various chemical reaction conditions. For example, prolific journal articles and patent literatures introducing zeolite synthesis offer a vast amount of data as historical information. The input data 102 and training data 104 can be retrieved from tables, figures, and experimental descriptions of those documents by using automatic data extracting techniques, e.g., natural language processing or text parsing tools. A more detailed description of the data extraction from historical information will be provided in FIGS. 2-4.

In an example embodiment, a training dataset 104 is sent to the catalyst design framework 108 to train the ML algorithm 114 for catalyst chemical reaction prediction. The training dataset 104 is the one used to train the ML algorithm 116 in understanding how the chemical reactions start and perform, and in applying relevant principles to the deep learning neural network 116 to learn and produce resulting catalyst production yield 110 accordingly. In this example, the workflow 100 also includes providing prediction dataset 106 which is used to evaluate how well the catalyst design framework 108 is trained based on the training dataset 104. Here, the prediction dataset 106 may be derived from the historical information 102 and forecast the performance of the chemical reactants and conditions. The training data 104 and the prediction data 106 may represent 80% and 20% of the overall data retrieved from the historical information 102, respectively.

In an example embodiment, the workflow 100 includes the catalyst design framework 108 that is configured to generate catalyst production yield prediction models for the catalyst construction. As shown in FIG. 1, the catalyst design framework 108 includes the ML algorithm 114 that is trained through the deep learning neural network 116. In this example, the deep learning neural network 116 may be a vectorized cognitive deep learning network which utilizes vector representations of chemical reactions in forms of text data and graphic data in the deep learning. The ML algorithm 114 may include a supervised learning approach that builds a mathematical model of a set of variables containing both the inputs and desired outputs. Through the training of the model, the supervised ML algorithm learns a function that can be used to predict the output associated with the input variables. Here, the supervised ML algorithm may be continuously trained until achieving improved accuracy of outputs or predictions over time. The deep learning neural network 116 may include an input layer and an output layer, as well as multiple intermediate hidden layers.

In an example embodiment, the workflow 100 includes a validation step 112 to estimate prediction accuracies of various resulting prediction models generated from the catalyst design framework 108. In this example, prediction data 106 are input to various prediction models and their comparison statistics, e.g., R-squared ($r^2$) statistics values, are calculated, respectively. The calculated comparison statistics values present a variety of "goodness-of-fit" statistics of the prediction models to the prediction data 106. In general, a higher comparison statistics value indicates a better fitting between the prediction model and the prediction data 106.

This invention generally relates to zeolite synthesis through chemical reaction design illustrated in the workflow 100. Zeolites are nanoporous, crystalline silica-based materials that feature a rich array of structures and at the present time there are up to hundreds of zeolite structures that have been determined. Moreover, the zeolite catalysts are primarily composed of corner-sharing $SiO_4$ tetrahedra, and may include heteroatoms such as Al, Ge, and P isomorphically substituted for the Si sites in zeolite. Because of their stable framework and versatile structure and composition, zeolite catalysts have been broadly used for many applications—especially in shape-selective transformations of hydrocarbons, and as molecular sieves for separating mixtures in the gas and oil industry.

Figure 2A:
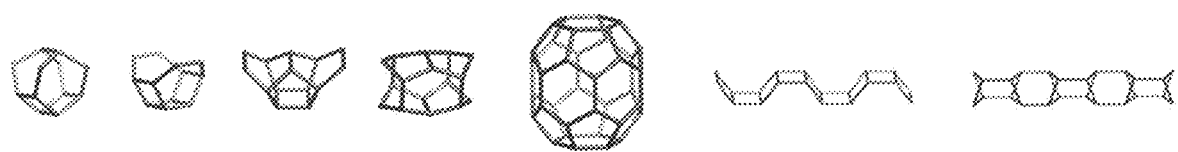
FIG. 2A illustrates example zeolite catalysts with various composite building blocks.
Figure 2B:
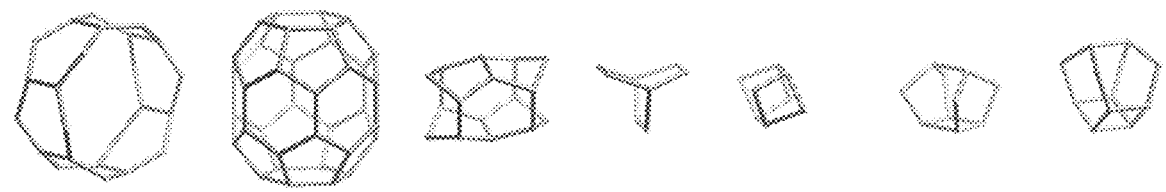
FIG. 2B illustrates example zeolite catalysts with various natural tilings.

Zeolite catalysts have unique combinations of pore openings ranging from ~3 Å to 10 Å, pore shape, and channel dimensionality that lead to a wide variety of zeolite framework structures. Those zeolite framework structures are always denoted by a 3-letter code, e.g., CHA, AFX, and AEI framework types. The hydrothermal stability and strong selective catalytic reduction (SCR) activity of zeolite catalysts are attributed to the architecture of their microporous frameworks, which is defined by careful selection of the overall pore architecture along with zeolite composition, cation substitution, and metal loading. The frameworks of zeolite catalysts are conventionally defined by their coordination sequences, composite building blocks, tiling, and transitivity information. FIGS. 2A and 2B illustrate exemplary zeolite catalysts with various composite building blocks and various natural tilings, respectively. For example, FIG. 2A discloses, from left to right, zeolite composite building units including ats (t-oh), afs, mel, imf, doh, dcc, and nsc. In addition, FIG. 2B discloses, from left to right, zeolite composite natural tilings including t-apf, t-doh, t-imf-7, t-kay, t-lov, t-mel, and t-oth.

The atlas of zeolite structures contains a collection of several dozen zeolite composite building blocks. As shown in FIG. 2A, an overwhelming majority of zeolite composite building blocks are cage-like objects centered on empty space including double 4-ring and double 6-ring motifs. There are many approaches to identifying zeolite building blocks including constructing atom centered environments as well as void-centered environments. The identified zeolite construction represents a natural extension of well-established approaches based on fragment decomposition of molecules and reflects the physical principle that macroscopic properties of materials arise from the combination of local atomic or molecular contributions. FIG. 2A shows various zeolite composite building blocks with different structures and environment energies. The hypothetical zeolites can be made by combining various zeolite composite building blocks or repeating the same zeolite composite building blocks in certain chemical reaction conditions. Particularly, zeolites with pores defined by 8 T-atoms that open into relatively large cages and framework structures with double 6-ring composite building blocks are known to perform well as catalysts in SCR.

The great variety of zeolite frameworks is caused not only by primary zeolite structural composite building blocks and their connection, but also by differences in connectivity of extended ensembles of the zeolite composite building blocks. Therefore, the tiling information became important in the description and taxonomy of zeolites. FIG. 2B illustrates example zeolite structures with various tiling information, indicating the complexity of the associated zeolite atomic network to teach zeolite framework types. Natural tiling is considered as a new type of zeolite building unit that has a number of advantages over other polyhedral building units. Zeolite natural tiling has been applied to find primitive cages in zeolite frameworks currently collected. In an example embodiment, the zeolite structure is completely composed by the zeolite natural tiles, wherein the zeolite natural tiles spread out all minimal cavities in the zeolite framework and all larger zeolite cages of its framework can be obtained by gluing the zeolite natural tiles.

Figure 3:
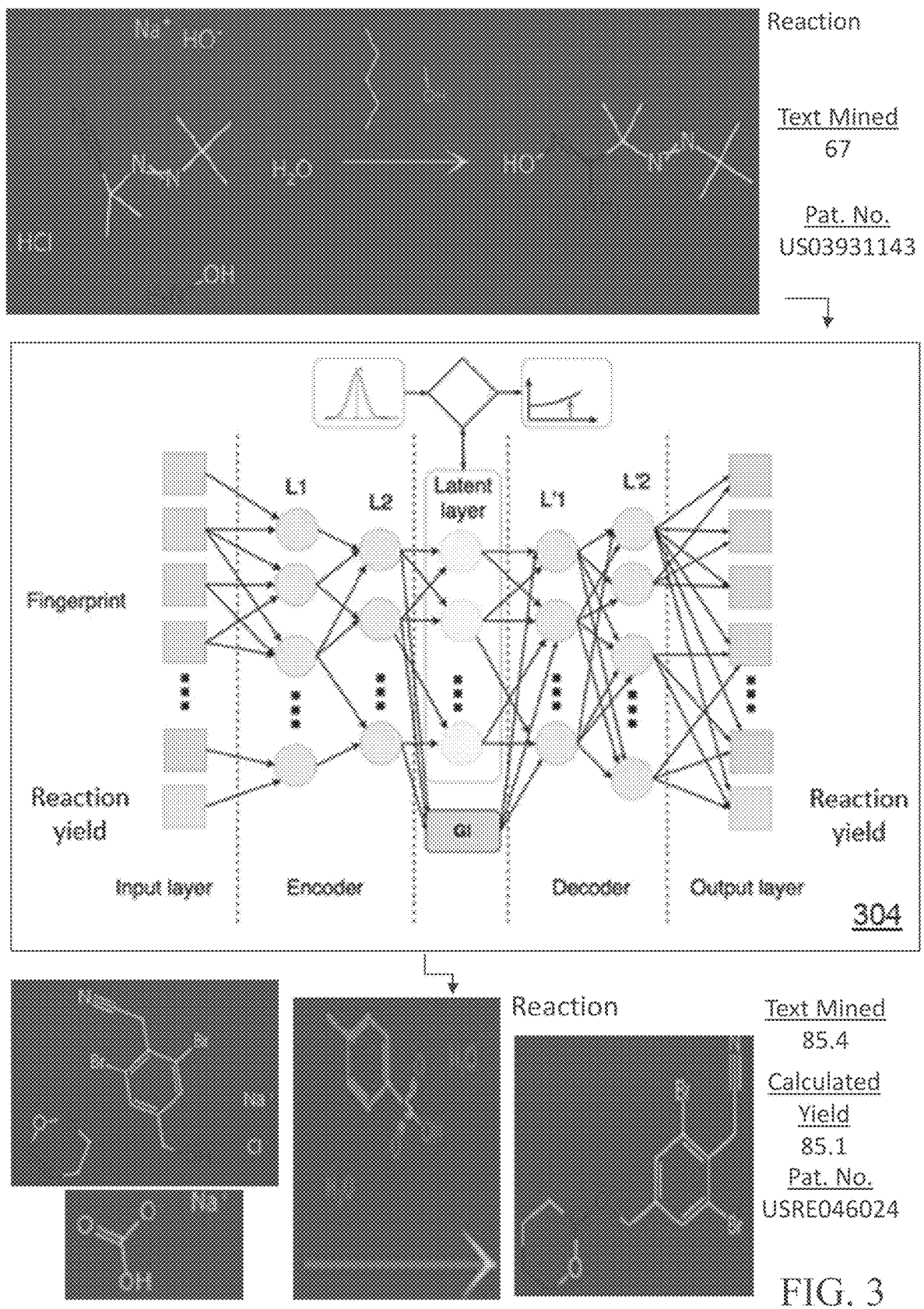
FIG. 3 illustrates an example workflow of creating catalyst formulations for catalyst construction.

FIG. 3 is an example workflow 300 of creating catalyst formulation, e.g., a zeolite catalyst formulation, for the zeolite catalyst construction. Referring to FIG. 1 and in an example embodiment, the example workflow 300 includes extracting input data from public and private catalyst reaction data for training the prediction models in the catalyst design framework 108 to predict the catalyst production yield. In this example, chemical reaction conditions, reactants, and synthesized product information are collected from patent reference U.S. Pat. No. 3,931,143, in step 302. This patent reference is publicly accessible and generally relates to unsymmetrical t-aliphatic alpha-cyano-azo alkanes, their derivatives, and processes for synthesizing. This reference describes a preparation of 2-t-Butylazo-2-methylpropionamidoxime by mixing 0.12 moles of hydroxylamine hydrochloride and 0.12 moles of 50% NaOH in 90% aqueous methanol. The mixture was stirred for 72 hours at room temperature poured into 400 ml of water and extracted with 100 ml of methylene chloride. The final product is formed with a yield of 67%. The reactant materials, chemical reaction conditions, and the generated product, as well as the yield are text mined from this patent reference as shown in 302.

Next, in step 304, the extracted chemical reaction data including reactant materials and the resulting product are input into the deep learning neural network 116 to train a chemical reaction algorithm. As shown in the deep learning neural network of 304, classical neural net nodes are represented by circles in intermediate layers and blocks in input and output layers of the neural network. At the initial neural network layer, various training datasets including chemical reaction fingerprints and reaction yields are input into the neural net nodes of the initial layer. For example, the training data input into the neural network 306 may include the extracted chemical reaction information shown in step 302. The input training data also includes chemical reaction yield data corresponding to the reactants and products. Here, the input chemical reaction data is constructed into graph models to represent molecular structure data of the reactants and the resulting products.

As discussed earlier with respect to FIG. 1, the ML algorithm 114 is trained through the neural network of 304 to determine the best set of weights of each layer therein for enhancing a neural network model's prediction performance. The neural network shown in 304 can be trained without knowing precisely how training data propagates through from the initial input layers to a last output layer of the neural network. The number of nodes in each layer and the number of total neural net layers depend on a complexity of the prediction model. The deep neural network shown in 304 further includes converting of the production graph data to the catalyst production information including production synthesis recipes and processes performed by decoder layers L'1 and L'2 of the neural network. The training of the deep learning neural network of 304 generates a prediction model for predicting catalyst production yield.

Further, based on the generated prediction model, the workflow 300 validates the prediction model by using the prediction data 106 retrieved from historical information 102. Similar to the training data pulled from the patent reference in previous step 302, step 306 includes retrieving prediction data from another US patent reference titled as "Thyroid hormone analogs." As shown in step 306, the chemical reactants, chemical reaction conditions, and generated products are retrieved from the patent reference and input as data to the trained prediction model for validation. Moreover, the retrieved chemical reaction information is converted to graph information and molecular structure information for catalyst production yield prediction by the trained prediction model. In the example step 306, the retrieved resulting product yield is 85.4% according to text information mined from the patent reference. In contrast, the prediction model generates a calculated yield of 85.1% in accordance with input chemical reaction information retrieved from the patent reference. The workflow 300 may compare the calculated yield with the input yield for the comparison statistics, e.g., R-squared ($r^2$) statistics values, and determine that the predication model is accurate in predicting the catalyst production yield based on the comparison statistics value being smaller than a threshold value, e.g., 0.1.

Zeolite catalyst chemical reaction datasets can be pulled out from open access references. As illustrated in connection with FIGS. 1 to 3, catalyst chemical reaction information includes the reactants, chemical reaction conditions, and resulting products. Other information including chemical reaction steps, chemical reaction parameters, and organic structure directing agents associated with the chemical reaction steps also can be pulled from historical information 102. Exemplary chemical reaction information is shown below in Table 1.

TABLE 1

| Reference # | $SiO_2:Al_2O_3$ | Si:Ge | Si:Ti | $Na:SiO_2$ | $SDA1:SiO_2$ | SDA1 type | $SDA2:SiO_2$ |
|---|---|---|---|---|---|---|---|
| 1 | ∞ | ∞ | ∞ | 0 | 0.5 | 1,2,3,4,5-pentamethylimidazolium hydroxide | 0 |
| 2 | ∞ | ∞ | ∞ | 0 | 0.5 | 2-ethyl-1,3,4-trimethylimidazolium hydroxide | 0 |
| 3 | 8.3 | ∞ | ∞ | 0.3 | 0.16 | 3,3'-(butane-1,4-diyl)bis(1,2,4,5-tetramethylimidazolium) dihydroxide | 0 |
| 4 | ∞ | 2 | ∞ | 0 | 0.5 | 1,2-dimethyl-3-(4-methylbenzyl)imidazolium hydroxide | 0 |

| Reference # | SDA2 type | $HF:SiO_2$ | $H_2O:SiO_2$ | Temperature (°C.) | Time (d) | Result |
|---|---|---|---|---|---|---|
| 1 | — | 0.5 | 4 | 140 | 12 | STW |
| 2 | — | 0.5 | 14 | 140 | 70 | HPM-2 |
| 3 | — | 0 | 30 | 160 | 51 | CIT-8H |
| 4 | tetramethylammonium hydroxide pentahydrate | 0.5 | 5 | 160 | 14 | BEC |

Exemplary chemical reaction 1 discloses a method for making a StockholmUniversity-Thirty-Two (STW) structure zeolite by using an organic structure directing agent (SDA) of 1,2,3,4,5-pentamethylimidazolium hydroxide. This reference defines specific mole ratios between the reactants as $SDA1:SiO_2=0.5$, $HF:SiO_2=0.5$, $H_2O:SiO_2=4$, a chemical reaction temperature of 140° C., and a reaction time for 12 days.

In addition, exemplary chemical reaction 2 discloses another method for making a layered organosilicate HPM-2 structure zeolite by using an SDA of 2-ethyl-1,3,4-trimethylimidazolium hydroxide. This reference defines specific mole ratios between the reactants as $SDA1:SiO_2=0.5$, $HF:SiO_2=0.5$, $H_2O:SiO_2=14$, a chemical reaction temperature of 140° C., and a reaction time for 70 days.

Moreover, exemplary chemical reaction 3 discloses another method for making a CIT-8H framework structure zeolite by using an SDA of 3,3'-(butane-1,4-diyl) bis(1,2,4,5-tetramethylimidazolium) dihydroxide. This reference defines specific mole ratios between the reactants as $SiO_2:Al_2O_3=8.3$, $Na:SiO_2=0.3$, $SDA1:SiO_2=0.16$, $H_2O:SiO_2=30$, a chemical reaction temperature at 160° C., and a reaction time for 51 days.

Further, exemplary chemical reaction 4 discloses another method for making a BEC type zeolite by using an SDA1 of 1,2-dimethyl-3-(4-methylbenzyl)imidazolium hydroxide and an SDA2 of tetramethylammonium hydroxide pentahydrate. This reference defines specific mole ratios between the reactants as Si:Ge=2, SDA1:SiO$_2$=0.5, HF:SiO$_2$=0.5, H$_2$O:SiO$_2$=5, a chemical reaction temperature of 160° C., and a reaction time for 14 days.

Figure 4:
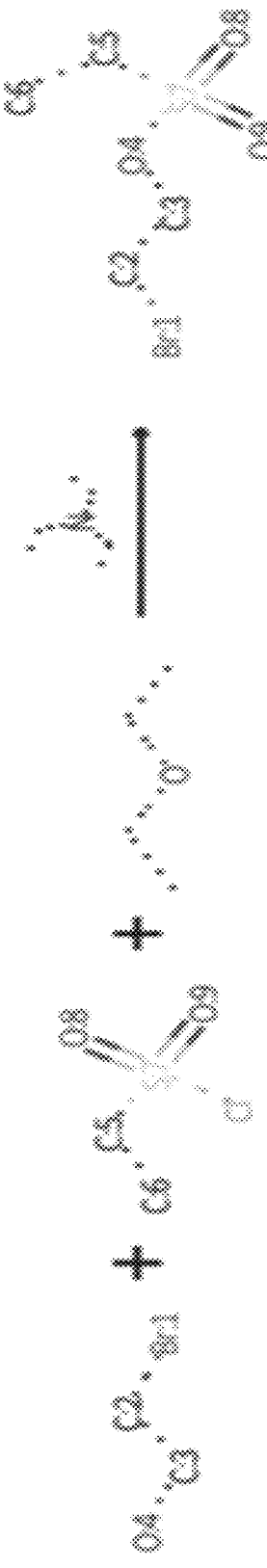
FIG. 4 illustrates example graph data for the training of the catalyst chemical reaction model.

FIG. 4 illustrates example graph data involved in the training of the catalyst chemical reaction model. Referring to FIGS. 1-3 and the previous corresponding description, the basic chemical reaction information encoded by molecular graphs is used as input to the neural network for training of a graph-based deep learning neural network. The neural network generalizes molecular graph data as a natural representation of chemical structures. More specifically, molecular graph data can be defined as connectivity relations between a set of nodes representing atoms and a set of edges representing chemical bonds.

Essentially, the neural network aims to learn the representations of each atom by aggregating information from its neighboring atoms and information from the connected chemical bonds. The neighboring atoms and connected bonds may be encoded, for example, by atom feature vectors and bond feature vectors, respectively. The molecular graph can be configured to include atomic features including atom symbol, atom degree, formal charge, hybridization, aromaticity, and chirality. Further, the molecular graph can be configured to include chemical bond features including chemical bond type, conjugation, ring, and stereo.

As shown in FIG. 4, the chemical reaction data 402 is extracted from accessible catalyst reaction data for training of the prediction models in the catalyst design framework 108. Here, a chemical reaction producing a zeolite is extracted from patent literature and shown as "[Br:1][CH2:2][CH2:3][OH:4].[CH2:5]([S:7](Cl)([O:9])=[O:8])[CH3:6].CCOCC>C(N(CC)C C)C>[CH2:5]([S:7]([O:4][CH2:3][CH2:2][Br:1])([O:9])=[O:8])[CH3:6]". This is a Simplified Molecular Input Line Entry System (SMILES) representation of the zeolite chemical reaction in a line notation. The SMILES notation consists of a series of characters containing no spaces. In addition, hydrogen atoms may be omitted or included in the SMILES notation.

SMILES is a chemical notation that allows a user to represent a chemical structure in a way that can be used by the computer. For example, with SMILES strings, a non-hydrogen atom is specified independently by its atomic symbol enclosed in square brackets. In addition, single, double, triple, and aromatic bonds are represented by the symbols "–", "=", "#", and ":", respectively. Adjacent atoms are assumed to be connected to each other by a single or aromatic bond. Further, various component parts of a chemical reaction are handled by introducing the ">" character to separate reactant, agent, and product. In this example, the agent for the zeolite chemical reaction is shown as C(N(CC)CC)C in the SMILES representation. In terms of a graph-based computational procedure, SMILES strings are obtained by printing the symbol nodes encountered in a depth-first tree traversal of a chemical graph. The chemical graph is firstly trimmed to remove hydrogen atoms and cycles are broken to turn it into a spanning tree. Numeric suffix labels are also included to indicate the connected nodes.

Standard tools can be utilized to parse and visualize the SMILES representation of chemical reactions. In this example, the zeolite chemical reaction is computed in Python with RDkit. The generated zeolite chemical reaction visualization, shown in 404, reveals chemical structures of the reactants, agent, and zeolite product, according to extracted chemical reaction data shown in SMILES format.

Moreover, graphs of individual molecules may be constructed based on the chemical reaction visualization result. In this example, the molecule graph construction 406 shows graphs of a reactant ethyl ether for the zeolite chemical reaction. The ethyl ether has a molecular formula of C$_4$H$_{10}$O and is extracted from reference literature as a reactant of a zeolite chemical reaction. The ethyl ether is further converted into "CCOCC" in the SMILES representation and is constructed in molecular graphs as shown in 406a and 406b. In this example, the molecule graph construction 406 shows the molecule graph in two dimensions (in 406a) and three dimensions (in 406b). During the construction of the molecule graphs, a database of atomic properties is used for the node properties representation, and calculated or referenced chemical bond angles and intra-atomic properties are used for edge properties representation.

In an exemplary embodiment, these graphs of molecules involved in the chemical reaction are automatically generated, for example, using the SMILES format as input to the deep learning neural network 116. The molecule graph may be generated by the encoder layers L1 and L2 of the deep learning neural network 116, and input to the latent layer of the deep learning neural network 116 for training of the catalyst yield prediction models. On the other hand, the deep learning neural network 116 produces graph data for the product of the chemical reaction including production synthesis recipes and processes. The produced molecule graph data is further converted by the decoder layers, e.g., layers L'1 and L'2 of the deep learning neural network 116, and output in SMILES format.

Figure 5:
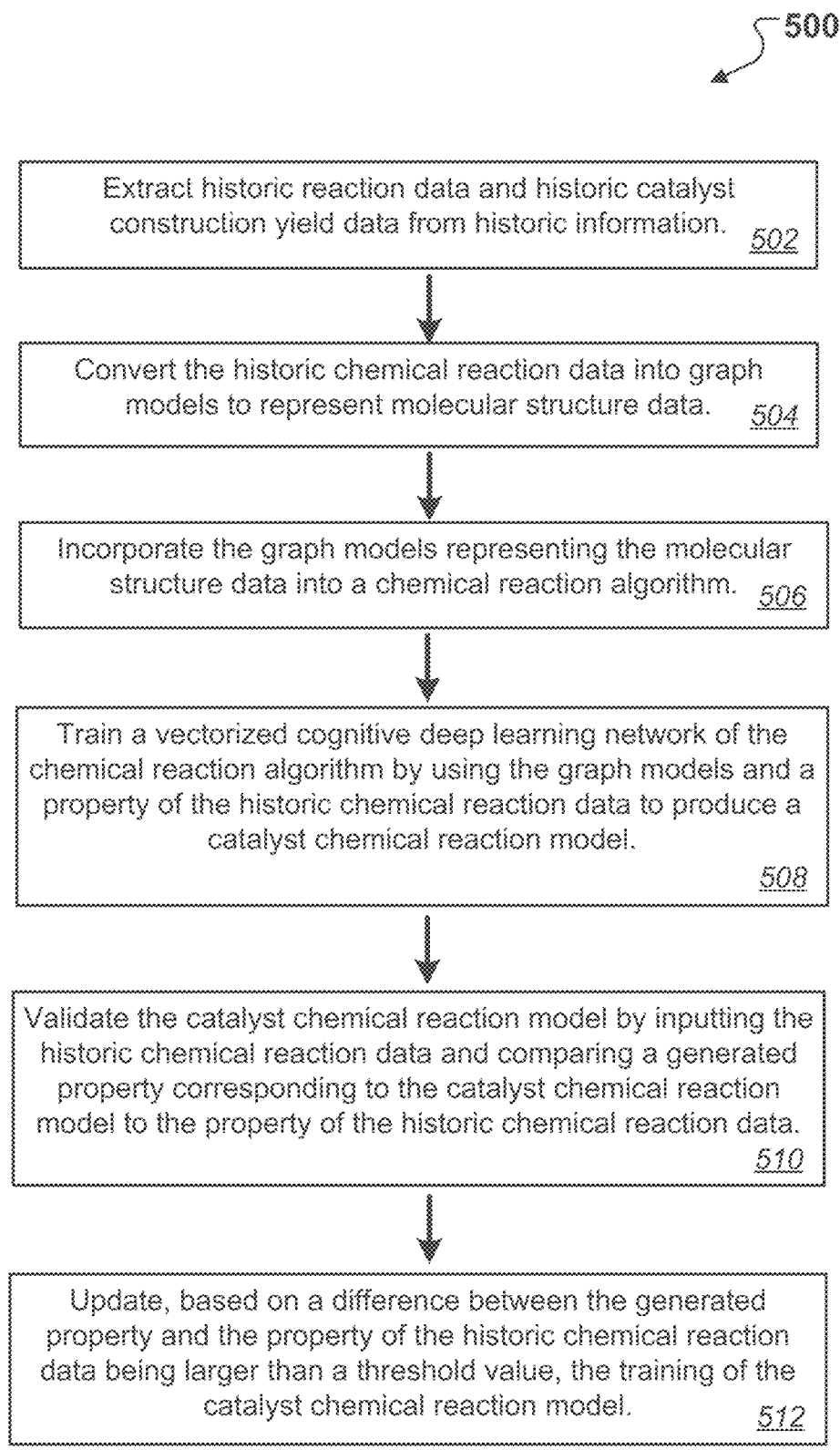
FIG. 5 illustrates an example method flow for designing chemical reactions for a catalyst construction.

FIG. 5 is an example method flow 500 for designing chemical reactions for a catalyst construction. Referring to FIGS. 1 to 4, and in an example embodiment, the method 500 includes extracting historic reaction data and historic catalyst construction yield data from historical information, at 502. The historical information can be collected from, for example, factory operation history, laboratory notes, operation log data, literature reports, or open access data sets and synthesis protocols that reveal catalyst production yield for various chemical reaction conditions. The historic reaction data can be retrieved, including reactants and mole ratios there between, chemical reaction conditions, SDA that assists the chemical reaction, and resulting products from the historical information. In addition, the catalyst construction yield data according to the historic reaction data can be pulled from the historical information. In some embodiments, advanced data extracting techniques, e.g., natural language processing and text parsing tools, are incorporated in this step to retrieve the historic reaction data and historic catalyst construction yield data from historical information in text, video, or audio formats. In some other embodiments, the historic reaction data and historic catalyst construction yield data correspond to the training data 104 described in FIG. 1.

The method flow also includes converting the historic chemical reaction data into graph models to represent molecular structure data, and incorporating the graph models into a chemical reaction algorithm, at 504 and 506 respectively. For example, the training data 104 including the historic chemical reaction data is converted into graph models before being input into the catalyst design framework 108. In an alternate example, historic chemical reaction data is input into the deep learning neural network 116 as training data and converted into graph models by the encoder layer of the deep learning neural network 116. The converted graph models representing molecular structure data are incorporated with the ML algorithm 114 for the catalyst construction.

Next, in step 508, the method flow 500 trains the vectorized cognitive deep learning network of the chemical reaction algorithm by using the graph models and any chemical, physical, or desired property of the chemical reaction to produce a catalyst chemical reaction model. For example, the deep learning neural network 116 may be a vectorized cognitive deep learning network which utilizes vector representations of chemical reactions in forms of text data and graphic data. The ML algorithm 114 includes a supervised learning approach that builds a mathematical catalyst chemical reaction model of a set of variables to predict desired output catalyst construction yield according to the input graph data and molecular structure data. Here, the ML algorithm may be continuously trained until achieving a desired accuracy of outputs or predictions over time.

The method flow 500 further includes validating the catalyst chemical reaction model by inputting the historic chemical reaction data and comparing a property generated corresponding to the catalyst chemical reaction or desired product or chemical to that of the historic chemical reaction data, at 510. For example, the prediction data 106 retrieved from historical information 102 is incorporated into the trained catalyst chemical reaction model for the validation. The prediction data 106 contains new historic chemical reaction data and new catalyst construction yield data that is retrieved from historical information and that corresponds to the new historic chemical reaction data. In this example, the validation step 510 compares the new catalyst construction yield data to a catalyst construction yield generated by the trained catalyst chemical reaction model according to the input of the new historical chemical reaction data. Lastly, the method flow 500 includes updating the training of the catalyst chemical reaction model when a difference between the calculated catalyst construction yield and the historic catalyst construction yield data is larger than a pre-defined threshold value, at 512. Otherwise, the catalyst chemical reaction model is validated based on the comparison statistics of the catalyst construction yield data being less than or equal to the pre-defined threshold value.

Figure 6:
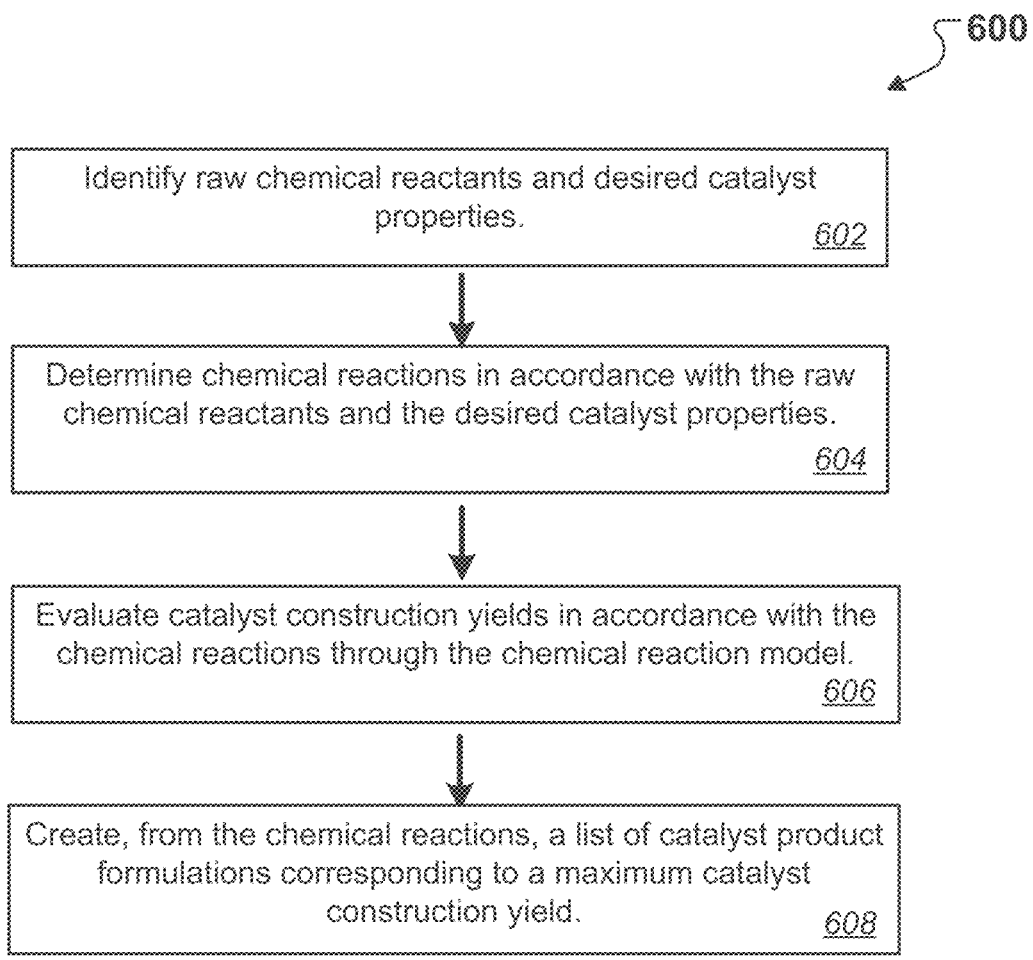
FIG. 6 illustrates an example method flow for creating catalyst formulations for a catalyst construction.

FIG. 6 is an example method flow 600 for creating catalyst formulations for a catalyst construction. Referring to FIGS. 1 to 5 and in an example embodiment, the method 600 includes identifying raw chemical reactants and desired catalyst properties, at 602. For example, the method 600 identifies raw chemical reactants that are available or in storage for the zeolite catalyst chemical reactions. Further, the identified raw chemical reactants are in accordance with zeolite catalysts having desired structures and physical properties. As described previously in table 1, the method 600 may identify raw chemical reactants including 1,2,3,4,5-pentamethylimidazolium hydroxide as an SDA, HF, $H_2O$, and $SiO_2$ for a catalyst chemical reaction targeting generation of a STW structure zeolite. In this example, the STW structure zeolite catalyst has a desired catalyst property of racemic conglomerates with decreasing strength as the length of the linker increases.

The method flow 600 also includes determining chemical reactions in accordance with the raw chemical reactants and the desired catalyst properties, at 604. Various chemical reactions formed at different temperatures and lasting for different durations may be determined based on the identified raw chemical reactants and desired catalyst properties. For example, when the raw chemical reactants are identified to include organic SDAs of 1,2,3,4,5-pentamethylimidazolium hydroxide and 2-ethyl-1,3,4-trimethylimidazolium hydroxide, $SiO_2$, HF, and $H_2O$, the method flow 600 determines that chemical reaction conditions of exemplary references 1 and 2 can be applied to the catalyst synthesis.

Further, the method flow 600 evaluates catalyst construction yields in accordance with the chemical reactions through the chemical reaction model, at 606. Specifically, catalyst construction yields are calculated through the trained catalyst chemical reaction model as discussed in FIG. 1. Here, the determined chemical reactions data including raw chemical reactants, chemical reaction conditions, and organic structure directing agents are first converted into graph data and molecular structure data and then input to the trained catalyst chemical reaction model for catalyst construction yield calculation.

Last, the method flow 600 includes creating a list of catalyst product formulations corresponding to a maximum catalyst construction yield from the chemical reactions, at 608. In this step, the calculated catalyst construction yields and their corresponding catalyst products are collected and ranked in a certain order. Here, the catalyst formulations are generated with a beam search algorithm. The catalyst construction yields are calculated by the trained catalyst chemical reaction model and the top yields/selective catalyst formulations are saved for reporting. The order of the catalyst products is based on the highest model predicted yields. The listed catalyst formulations display catalyst products that can be synthesized from the identified raw chemical reactants and that reveal the desired catalyst properties.

Figure 7:
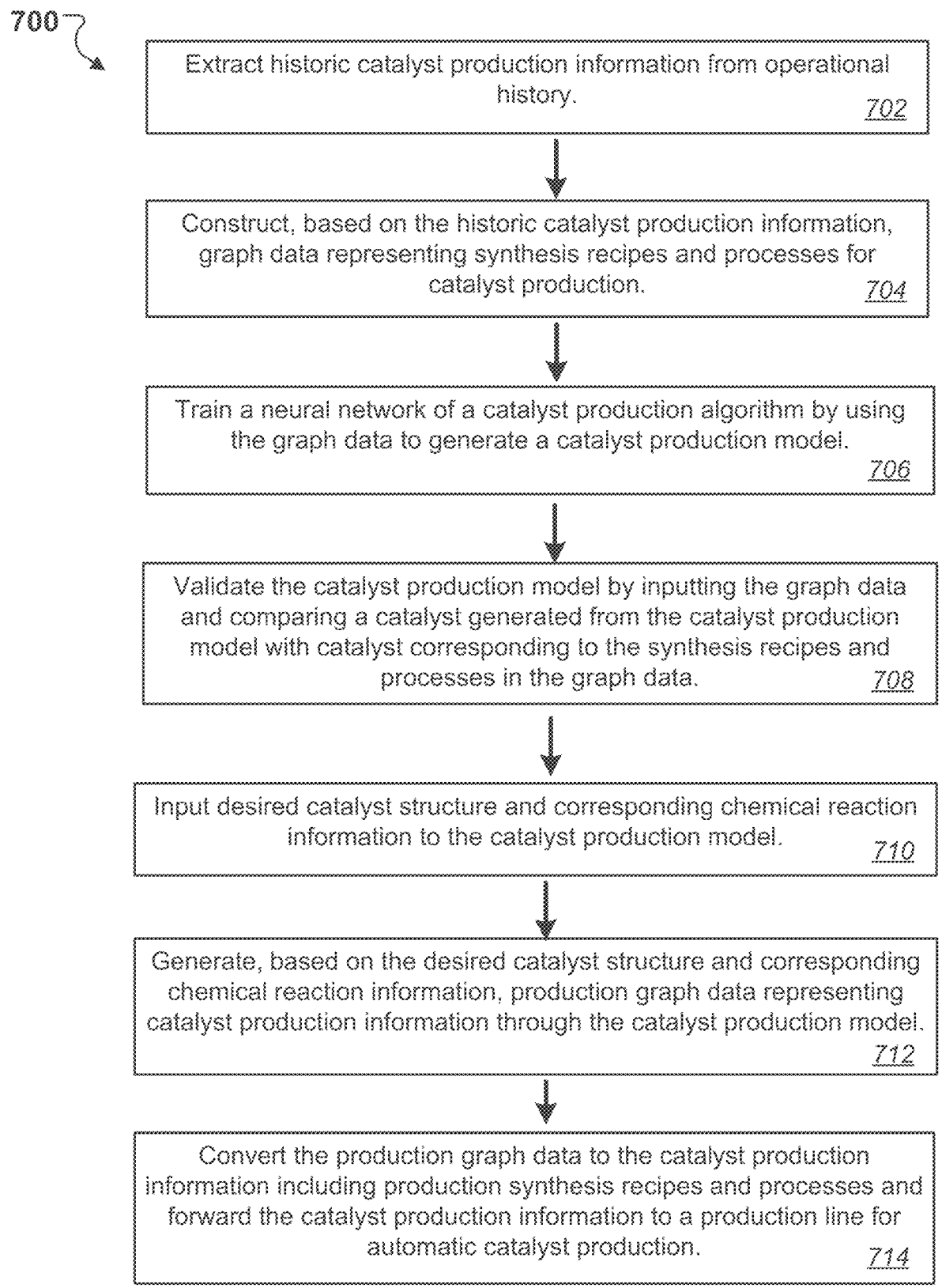
FIG. 7 illustrates an example method flow for constructing a catalyst structure.

FIG. 7 is an example method flow 700 for constructing a catalyst product. Referring to FIGS. 1 to 6 and in an example embodiment, the method 700 includes extracting historic catalyst production information from operational history, at 702. For example, zeolite catalyst construction data may be extracted from factory operation history, laboratory notes, operation log data, literature reports, or open access zeolite synthesis protocols that reveal historical zeolite construction data. The zeolite catalyst construction data may include the raw reactants, chemical reaction conditions, operation procedures and protocols, equipment involved in the chemical reaction, and resulting zeolite products formulations and structures. For example, exemplary historic catalyst production information can be pulled from production history. It may reveal raw reactants including initial gel and silica, equipment including magnetic stirrer and bakers, operation procedures including stirring, ageing, microwave treatment and hydrothermal treatment, chemical reaction conditions including reaction temperature and durations for each procedure, and the resulting zeolite structure.

The method flow 700 also includes constructing, based on the historic catalyst production information, graph data representing synthesis recipes and processes for catalyst production, at 704. Once the historic catalyst production information is extracted, it is further constructed into graph data with nodes to represent the catalyst synthesis steps, parameters, as well as organic structure directing agents in related steps. For example, the zeolite synthesis processes including stirring, ageing, microwave treatment and hydrothermal treatment each can be constructed into a node shown in large circles. In addition, small circles can be attached to each of the nodes representing raw reactants, chemical reaction conditions, or organic structure directing agent information related to the corresponding processing steps. In particular, the small circles attached to the last reaction step represent the resulting zeolite structure and formulation information. In some embodiments, the constructing of the graph data is performed by an encoding layer of a neural network, e.g., the deep learning neural network 116 shown in FIG. 1.

In addition, the method flow 700 includes training a neural network of a catalyst production algorithm by using the graph data to generate a catalyst production model, at 706. In this step, the catalyst production model is trained through a neural network that is connected to the catalyst production algorithm, e.g., the deep learning neural network 116, by inputting the constructed graph data to the neural network. The graph data input to the neural network is originated from the extracted historic catalyst production information, as training data 104 discussed in FIG. 1. Here, the catalyst production model may include a set of variables and weights to predict the catalyst product in accordance with the input catalyst production information. The catalyst production algorithm is continuously trained until achieving improved accuracy of outputs of the catalyst production.

Further, the method flow 700 includes validating the catalyst production model by inputting the graph data and comparing a catalyst generated from the catalyst production model with catalyst corresponding to the synthesis recipes and processes in the graph data, at 708. The validating is conducted by inputting a new set of historic chemical reaction data to the trained catalyst production model and comparing the resulting catalyst product to the catalyst product corresponding to the input historic chemical reaction data. The new set of historic chemical reaction data may be additionally extracted from historic information, or a portion of the historic reaction data extracted in step 502. Similar to the training data input to the neural network discussed in step 508, the new set of historic chemical reaction data is constructed into graph data representing catalyst synthesis recipes, chemical reaction processes, and resulting catalyst product formulations and structures. The catalyst production model is validated based on the comparison statistics of the catalyst products being less than or equal to the pre-defined threshold value.

After the catalyst production model is generated by the catalyst production algorithm discussed in the previous steps, the method flow 700 inputs desired catalyst structure and corresponding chemical reaction information into the catalyst production model, at 710. The desired catalyst structure and corresponding chemical reactions information can be collected from the catalyst formulations creating procedures described in FIG. 6. For example, when a STW framework structure zeolite catalyst is identified as the desired catalyst structure, the chemical reaction information including the raw reactants, chemical reaction conditions, and organic structure direct agents is generated through the trained chemical reaction model described in FIGS. 5 and 6.

In addition, the method flow 700 includes generating, based on the desired catalyst structure and corresponding chemical reaction information, production graph data representing catalyst production information through the catalyst production model, at 712. For example, based on the input STW framework zeolite catalyst structure information and corresponding stirring, ageing, microwave and hydrothermal treatments synthesis procedures described earlier, the catalyst production model generates production graph data representing the catalyst production information including the raw reactants, synthesis recipes, chemical reaction conditions for each procedure, and equipment that are necessary for the reactions.

Further, the method flow 700 converts the production graph data to the catalyst production information including production synthesis recipes and processes, at 714. As discussed earlier, the generated production graph data may include nodes in large circles representing the catalyst synthesis steps, parameters, as well as organic structure directing agents in related steps. The production graph data may also include small circles attached to each of the nodes representing raw reactants, chemical reaction conditions, or organic structure directing agent information related to the corresponding processing steps. In this step, the graph data is converted to catalyst production information, e.g., catalyst synthesis recipes and operation protocols, that production line equipment can recognize. Moreover, the converted catalyst production information is forwarded to the equipment located on the production line for automatic production of the desired catalyst product.

Figure 8:
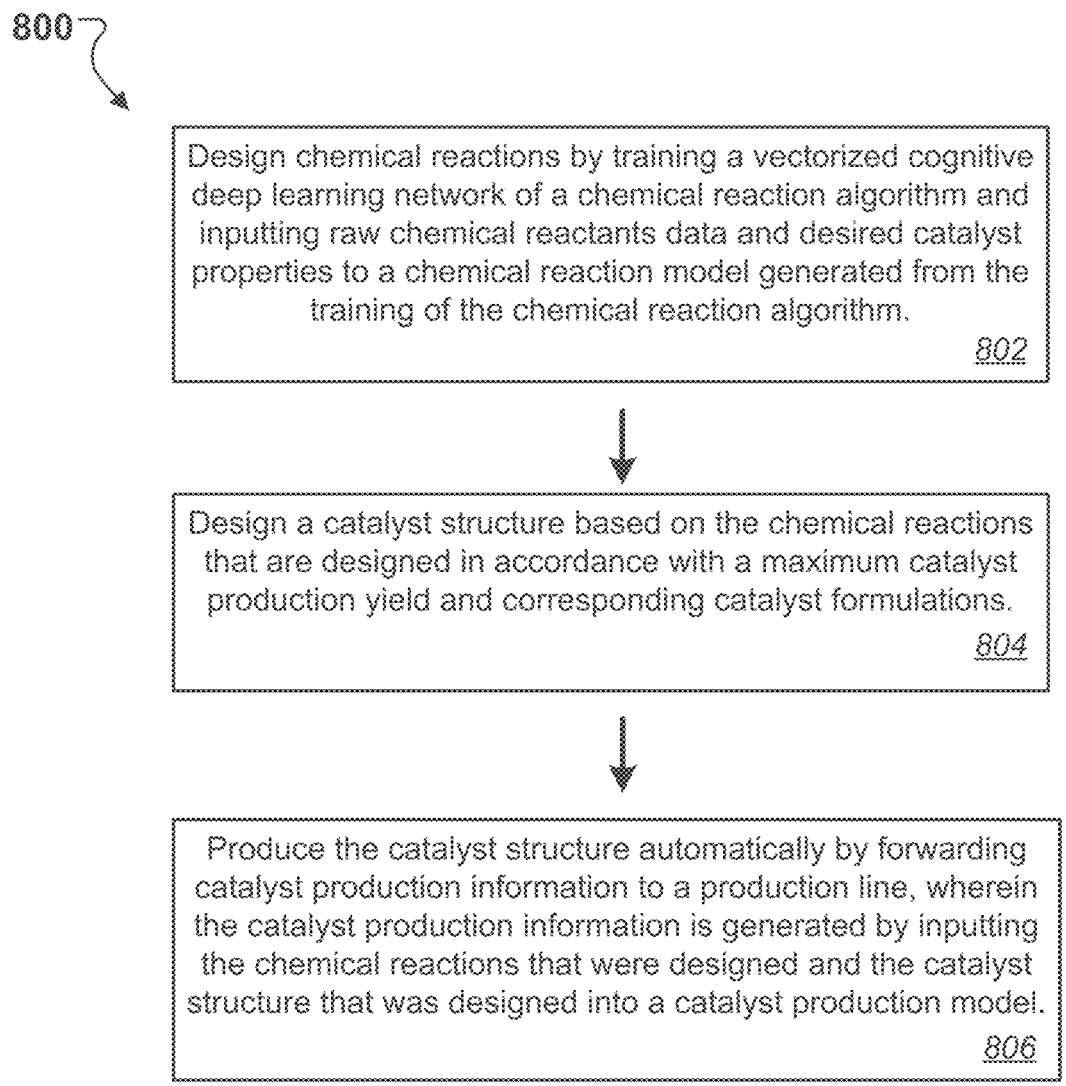
FIG. 8 illustrates an example method flow of AI assisted catalyst processing.

FIG. 8 is an example method flow 800 of artificial intelligence assisted catalyst processing. Referring to FIGS. 1 to 7 and in an example embodiment, the method 800 starts from designing chemical reactions by training a vectorized cognitive deep learning neural network of a chemical reaction algorithm and inputting raw chemical reactant data and desired catalyst product properties to a chemical reaction model generated from the training of the chemical reaction algorithm, at 802. The chemical reactions and corresponding catalyst construction yields are extracted from historical information for the training of the chemical reaction algorithm to generate the chemical reaction model. Specifically, the training of the chemical reaction algorithm includes converting the raw chemical reactants data and desired catalyst product properties to graph data and inputting the graph data into the vectorized cognitive deep learning neural network for training. In addition, a list of catalyst product formulations is created, the list being configured to include catalyst construction yield and chemical reactions corresponding to the catalyst product formulations.

The method flow 800 further designs a catalyst structure based on the chemical reactions that are designed in accordance with at least one of a production yield, selectivity, desired property, or corresponding catalyst product formulations, at 804. In this step, the method flow 800 may evaluate catalyst construction yields of catalyst product formulation shown on the list. For example, a STW type zeolite catalyst with a construction yield of 67% is ranked on top of the list and is evaluated as the catalyst with a maximum catalyst production yield. The structure of the STW type zeolite catalyst is further designed in accordance with the chemical reactions corresponding to the maximum catalyst production yield.

Moreover, the method flow 800 produces the catalyst structure automatically by forwarding catalyst production information to a production line, wherein the catalyst production information is generated by inputting the chemical reactions that were designed and the catalyst structure that was designed into a catalyst production model, at 806. Here, the catalyst production model is generated by training of a deep learning neural network of a catalyst production algorithm. The training of the catalyst production algorithm includes inputting historical catalyst production information extracted from historic information and validating the catalyst production model until the catalyst production model provides a good prediction of catalyst product corresponding to the catalyst production information. The catalyst production information generated from the catalyst production model is in the form of graph data. This step 806 first converts the graph data into catalyst production synthesis recipes and processes information and then forwards the catalyst production synthesis recipes and process information to a production line for automatic catalyst production.

Figure 9:
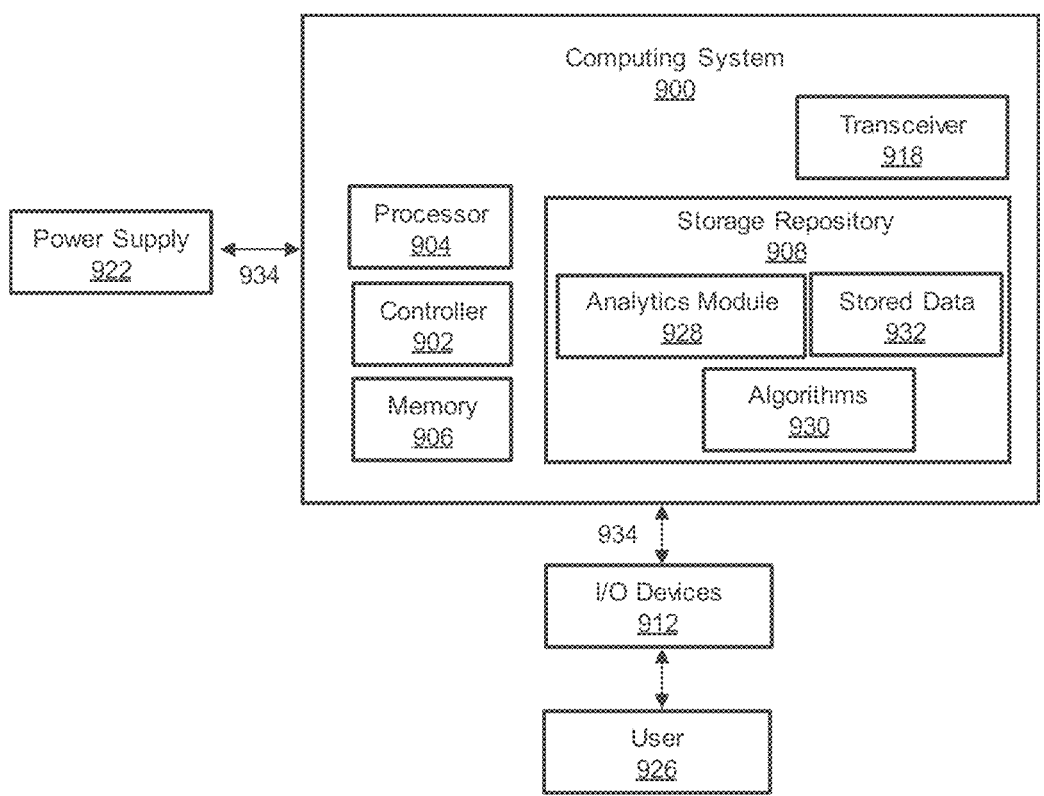
FIG. 9 illustrates a block diagram of an example system for zeolite catalyst synthesis directed by the machine learning algorithm.

FIG. 9 is a block diagram of an example system 900 for zeolite catalyst synthesis directed by the ML approaches described previously. The system 900 comprises a computer 900 with a controller 902, a processor 904, a memory 906, a transceiver 918 and a storage repository 908 which can comprise an analytics software module 928, stored data 932, and algorithms 930. The transceiver 918 can send and receive data. The analytics software module 928 can be implemented as computer readable instructions stored in memory. The analytics software module 928 can perform the methods described herein and can render a graphical user interface in the form of a catalyst chemical reaction prediction analytics dashboard described in connection with FIGS. 1-8. Input and output devices 912 are connected to the computer 900 through wired or wireless means 934. The computer 900 can receive power from a power supply 922. A bus (not shown) can allow the various components and devices to communicate with one another. A bus can be one or more of any of several types of bus structures, including a memory bus or memory controller, a peripheral bus, an accelerated graphics port, and a processor or local bus using any of a variety of bus architectures. A bus can include wired and/or wireless buses. The components shown in FIG. 9 are not exhaustive, and in some embodiments, one or more of the components shown in FIG. 9 may not be included in a specific embodiment. Further, one or more components shown in FIG. 9 can be rearranged. It should also be understood that in embodiments, the various elements shown here can be located together or located remotely from each other. For example, the storage repository could be stored in a different location, such as on a server, from the processor used by the computing system.

The methods described herein can be implemented with software and executed by one or more processors. Generally, software includes routines, programs, objects, components, data structures, and so forth that perform particular tasks or implement particular abstract data types. An implementation of these modules and techniques can be stored on or transmitted across some form of computer readable media. Computer readable media is any available non-transitory medium or non-transitory media that is accessible by a computing device. By way of example, and not limitation, computer readable media includes computer storage media.

Systems of the disclosure can include an intranet-based computer system that is capable of communicating with various software. A computer system includes any type of computing device and/or communication device. Examples of such a system can include, but are not limited to, super computers, a processor array, a distributed parallel system, a desktop computer with LAN, WAN, Internet or intranet access, a laptop computer with LAN, WAN, Internet or intranet access, a smart phone, a server, a server farm, an android device (or equivalent), a tablet, smartphones, and a personal digital assistant (PDA). Further, as discussed above, such a system can have corresponding software (e.g., graphical user interface software, analytics software). The software of one system can be a part of, or operate separately but in conjunction with, the software of another system.

Embodiments of the disclosure include a storage repository. The storage repository can be a persistent storage device (or set of devices) that stores software and data. Examples of a storage repository can include, but are not limited to, a hard drive, flash memory, some other form of solid-state data storage, or any suitable combination thereof. The storage repository can be located on multiple physical machines, each storing all or a portion of a database, protocols, algorithms, software modules, and/or other stored data according to some example embodiments. Each storage unit or device can be physically located in the same or in a different geographic location. In embodiments, the storage repository may be stored locally, or on cloud-based servers such as Amazon Web Services.

In one or more example embodiments, the storage repository stores one or more databases, AI Platforms, protocols, algorithms, software modules, and stored data. The protocols can include any of a number of communication protocols that are used to send and/or receive data between the processor, datastore, memory and the user. A protocol can be used for wired and/or wireless communication. Examples of protocols can include, but are not limited to, Modbus, profibus, Ethernet, and fiberoptic.

Systems of the disclosure can include a hardware processor. The processor executes software, algorithms, and firmware in accordance with one or more example embodiments. The processor can be a central processing unit, a multi-core processing chip, SoC, a multi-chip module including multiple multi-core processing chips, or other hardware processor in one or more example embodiments. The processor is known by other names, including but not limited to a computer processor, a microprocessor, and a multi-core processor. The processor can also be an array of processors.

In one or more example embodiments, the processor executes software instructions stored in memory. Such software instructions can include performing analysis on data received from the database and so forth. The memory includes one or more cache memories, main memory, and/or any other suitable type of memory. The memory can include volatile and/or non-volatile memory.

The processing system can be in communication with a computerized data storage system which can be stored in the storage repository. The data storage system can include a non-relational or relational data store, such as a MySQL or other relational database. Other physical and logical database types could be used. The data store may be a database server, such as Microsoft SQL Server, Oracle, IBM DB2, SQLITE, or any other database software, relational or otherwise. The data store may store the information identifying syntactical tags and any information required to operate on syntactical tags. In some embodiments, the processing system may use object-oriented programming and may store data in objects. In these embodiments, the processing system may use an object-relational mapper (ORM) to store the data objects in a relational database. The systems and methods described herein can be implemented using any number of physical data models. In one example embodiment, an RDBMS can be used. The tables of the RDBMS can have pre-defined relationships between them.

In embodiments, the systems of the disclosure can include one or more I/O (input/output) devices that allow a user to enter commands and information into the system, and also allow information to be presented to the user and/or other components or devices. Examples of input devices include, but are not limited to, a keyboard, a cursor control device (e.g., a mouse), a microphone, a touchscreen, and a scanner. Examples of output devices include, but are not limited to, a display device (e.g., a display, a monitor, or projector), speakers, a printer, and a network card.

For any figure shown and described herein, one or more of the components may be omitted, added, repeated, and/or substituted. Accordingly, embodiments shown in a particular figure should not be considered limited to the specific arrangements of components shown in such figure. Further, if a component of a figure is described but not expressly shown or labeled in that figure, the label used for a corresponding component in another figure can be inferred to that component. Conversely, if a component in a figure is labeled but not described, the description for such component can be substantially the same as the description for the corresponding component in another figure.

Although particular embodiments have been described herein in detail, the descriptions are by way of example. The features of the embodiments described herein are representative and, in alternative embodiments, certain features, elements, and/or steps may be added or omitted. Additionally, modifications to aspects of the embodiments described herein may be made by those skilled in the art without departing from the scope of the following claims, the scope of which are to be accorded the broadest interpretation so as to encompass modifications and equivalent structures.

What is claimed is:

1. A computer implemented method for catalyst construction, the method comprising:
   extracting historical data including historic chemical reaction data and historic catalyst construction yield data;
   converting the historic chemical reaction data into graph models to represent molecular structure data;
   incorporating the graph models representing the molecular structure data into a chemical reaction algorithm;
   training a vectorized cognitive deep learning network of the chemical reaction algorithm by using the graph models and a property of the historic chemical reaction data to produce a catalyst chemical reaction model;
   validating the catalyst chemical reaction model by inputting the historic chemical reaction data and comparing a generated property corresponding to the catalyst chemical reaction model to the property of the historic chemical reaction data; and
   updating, based on a difference between the generated property and the property of the historic chemical reaction data being larger than a threshold value, the training of the catalyst chemical reaction model.

2. The computer implemented method of claim 1, further comprising:
   identifying raw chemical reactants and desired catalyst properties;
   determining chemical reactions in accordance with the raw chemical reactants and the desired catalyst properties;
   evaluating catalyst construction yields in accordance with the chemical reactions through the chemical reaction model; and
   creating, from the chemical reactions, a list of catalyst formulations corresponding to a maximum catalyst construction yield.

3. The computer implemented method of claim 1, wherein the graph models include nodes representing atoms with specific molecular properties and vertices representing intermolecular properties, wherein the molecular properties include atom surface area, atom volume, and atom surface energy, and wherein the intermolecular properties represented by the vertices include chemical bond type and chemical bond angle.

4. The computer implemented method of claim 3, wherein the nodes included in the graph models also represent chemical reaction steps, chemical reaction parameters, and organic structure directing agents in related chemical reaction steps.

5. The computer implemented method of claim 2, further comprising designing of catalyst chemical structures based on the chemical reactions and the catalyst formulations.

6. The computer implemented method of claim 5, wherein the catalyst chemical structures reveal topological, geometrical, and tiling information of the catalyst.

7. The computer implemented method of claim 2, wherein the catalyst formulations are created in accordance with a minimum catalyst construction yield.

8. The computer implemented method of claim 1, wherein the historic chemical reaction data and the historic catalyst construction yield data are extracted from historic information including literature reports, experiment notes, and manufacturing records.

9. The computer implemented method of claim 1, further comprising designing of chemical reactions for producing a zeolite.

10. A computer implemented method for constructing a catalyst structure, the method comprising:
    extracting historic catalyst production information from operational history;
    constructing, based on the historic catalyst production information, graph data representing synthesis recipes and processes for catalyst production;
    training a neural network of a catalyst production algorithm by using the graph data to generate a catalyst production model; and
    validating the catalyst production model by inputting the graph data and comparing a catalyst generated from the catalyst production model with catalyst corresponding to the synthesis recipes and processes in the graph data.

11. The computer implemented method of claim 10, further comprising:
    inputting desired catalyst structure and corresponding chemical reaction information into the catalyst production model;
    generating, based on the desired catalyst structure and corresponding chemical reaction information, production graph data representing catalyst production information through the catalyst production model;
    converting the production graph data to the catalyst production information including production synthesis recipes and processes; and
    forwarding the catalyst production information to a production line for automatic catalyst production.

12. The computer implemented method of claim 11, wherein the corresponding chemical reaction information is designed by:
    extracting historical data including historic chemical reaction data and historic catalyst construction yield data;
    converting the historic chemical reaction data into reaction graph data and molecular structure data;
    incorporating the reaction graph data and the molecular structure data into a chemical reaction algorithm;
    training a vectorized cognitive deep leaning network of the chemical reaction algorithm by using the reaction graph data, molecular structure data, and historic catalyst construction yield data to produce a catalyst chemical reaction model;
    validating the catalyst chemical reaction model by inputting the historic chemical reaction data and comparing a calculated catalyst construction yield generated by the chemical reaction model to the historic catalyst construction yield data; and
    updating, based on a difference between the calculated catalyst construction yield and the historic catalyst construction yield data being larger than a threshold value, the training of the catalyst chemical reaction model.

13. The computer implemented method of claim 12, further comprising:
   identifying raw chemical reactants and desired catalyst properties;
   determining chemical reactions in accordance with the raw chemical reactants and the desired catalyst properties;
   evaluating catalyst construction yields in accordance with the chemical reactions through the chemical reaction model; and
   creating, from the chemical reactions, a list of catalyst formulations corresponding to a maximum catalyst construction yield.

14. The computer implemented method of claim 13, wherein the desired catalyst structure is constructed based on the chemical reactions and catalyst product formulations, and wherein the production line includes a robotic arm, ingredients, and production equipment.

15. The computer implemented method of claim 11, wherein the constructing of the graph data representing synthesis recipes and processes is performed by an encoder of the neural network.

16. The computer implemented method of claim 11, wherein the converting of the production graph data to the catalyst production information including production synthesis recipes and processes is performed by a decoder of the neural network.

17. The computer implemented method of claim 10, wherein the historic catalyst production information can be further extracted from literature reports.

18. An artificial intelligence assisted catalyst processing method implemented by a computer, the method comprising:
   designing chemical reactions by training a vectorized cognitive deep learning network of a chemical reaction algorithm and inputting raw chemical reactants data and desired catalyst product properties to a chemical reaction model generated from the training of the chemical reaction algorithm;
   designing a catalyst structure based on the chemical reactions that are designed in accordance with a maximum catalyst production yield and corresponding catalyst product formulations; and
   producing the catalyst structure automatically by forwarding catalyst production information to a production line, wherein the catalyst production information is generated by inputting the chemical reactions that were designed and the catalyst structure that was designed into a catalyst production model.

19. The artificial intelligence assisted catalyst processing method of claim 18, wherein the training of the vectorized cognitive deep learning network of the chemical reaction algorithm further includes:
   extracting historical data including historic chemical reaction data and historic catalyst construction yield data;
   converting the historic chemical reaction data into graph models to represent molecular structure data;
   incorporating the graph models representing the molecular structure data into a chemical reaction algorithm;
   training a vectorized cognitive deep learning network of the chemical reaction algorithm by using the graph models and a property of the historic chemical reaction data to produce a catalyst chemical reaction model;
   validating the catalyst chemical reaction model by inputting the historic chemical reaction data and comparing a generated property corresponding to the catalyst chemical reaction model to the property of the historic chemical reaction data; and
   updating, based on a difference between the generated property and the property of the historic chemical reaction data being larger than a threshold value, the training of the catalyst chemical reaction model.

20. The artificial intelligence assisted catalyst processing method of claim 18, wherein the producing of the catalyst structure automatically further includes:
   extracting historic catalyst production information from operational history;
   constructing, based on the historic catalyst production information, graph data representing synthesis recipes and processes for catalyst production;
   training a neural network of a catalyst production algorithm by using the graph data to generate the catalyst production model; and
   validating the catalyst production model by inputting the graph data and comparing a catalyst generated from the catalyst production model with catalyst corresponding to the synthesis recipes and processes in the graph data.

* * * * *